(12) United States Patent
Depfenhart

(10) Patent No.: US 10,258,506 B2
(45) Date of Patent: Apr. 16, 2019

(54) LASER THERAPY SYSTEM FOR NONINVASIVE CORRECTION OF THE REFRACTIVE SYSTEM OF THE EYE

(71) Applicant: Telesto GmbH, Ulm (DE)

(72) Inventor: Markus Depfenhart, Hamburg (DE)

(73) Assignee: TELESTO GMBH, Ulm (DE)

( * ) Notice: Subject to any disclaimer, the term of this patent is extended or adjusted under 35 U.S.C. 154(b) by 1208 days.

(21) Appl. No.: 14/133,688

(22) Filed: Dec. 19, 2013

(65) Prior Publication Data
US 2014/0171927 A1 Jun. 19, 2014

(30) Foreign Application Priority Data
Dec. 19, 2012 (EP) .................................. 12197973

(51) Int. Cl.
*A61F 9/008* (2006.01)
*A61N 5/06* (2006.01)
*A61F 9/007* (2006.01)

(52) U.S. Cl.
CPC .......... *A61F 9/00804* (2013.01); *A61F 9/008* (2013.01); *A61F 9/0079* (2013.01); *A61N 5/062* (2013.01); *A61F 2009/00851* (2013.01); *A61F 2009/00853* (2013.01); *A61F 2009/00865* (2013.01); *A61F 2009/00872* (2013.01); *A61N 2005/0661* (2013.01)

(58) Field of Classification Search
CPC .... A61F 9/00804; A61F 9/0079; A61F 9/008; A61F 2009/00851; A61F 2009/00853; A61F 2009/00865; A61F 2009/00872; A61N 5/062; A61N 2005/0661
USPC ............................................................. 606/5
See application file for complete search history.

(56) References Cited

FOREIGN PATENT DOCUMENTS

| WO | 2002053050 | 7/2002 |
|---|---|---|
| WO | 2012/145159 | 10/2012 |
| WO | 2012158991 | 11/2012 |

*Primary Examiner* — Aaron F Roane
(74) *Attorney, Agent, or Firm* — Mark M. Friedman

(57) ABSTRACT

The present invention refers to a Laser therapy system and a method for a treatment of a cornea and/or sclera of an eye to correct its refractive system, comprising:
a dispenser for a photosensitizer agent;
a 3D imaging unit;
an image processing unit adapted to recognize a first collagen tissue structure and a first orientation of respective collagen fibers therein;
a UVA light source adapted to a crosslinking within the collagen tissue structure;
an optical system for deflecting and focusing the UVA light on a focus point behind an aperture within the imaging volume; and
a processing and control unit adapted to receive data relating to a refractive error of the eye, to determine a second collagen tissue structure with new corrective collagen crosslinks, such as to achieve a minimized refractive error of the eye and a UVA light energy to induce the new corrective collagen crosslinks.

14 Claims, 5 Drawing Sheets

LASER THERAPY SYSTEM FOR NONINVASIVE CORRECTION OF THE REFRACTIVE SYSTEM OF THE EYE

The present invention refers to a Laser therapy system and a method for a noninvasive correction of the refractive system of an eye, comprising a 3D imaging unit for imaging a collagen tissue structure of the cornea and/or sclera, a UVA light source with an optical deflection and focusing system and a processing and control unit to position a focus point of the UVA light precisely in the cornea and/or sclera.

BACKGROUND OF THE INVENTION

The cornea and sclera make up the outer tunic of the eye. Each is a connective tissue containing collagen fibrils embedded in a proteoglycan-rich extrafibrillar matrix, wherein the cornea is uniquely transparent and the sclera is totally opaque. Both tissues require strength to maintain the excess pressure within the eye and to resist external knocks and forces applied by extraocular muscles during eye movement. The mechanical strength is provided by deposition of collagen in a lamellar structure, wherein the lamellae run parallel to the surface of the tissue. The sclera as the white part of the eye is a tough connective tissue and is continuous with the cornea. Scleral collagen is, in composition and arrangement, similar to that of normal skin, with wider fibrils and much more interwoven structure than in the cornea. The sclera has no optical role other than to provide support for the retina on the back of the eye, but it has important physiological functions such as providing fluid outflow channels and mechanical functions such as maintaining an eye shape. The limbus constitutes the border between the cornea and the sclera. Changes of the collagen structure of the sclera and cornea are accompanied by a development of shortsightedness (myopia). The above-mentioned relationships are e.g. taught by K. M. Meek, Chapter 13, The Cornea and Sclera, pages 359 ff. of: P. Frantzl (ed.) Collagen Structure and Mechanics, Springer 2008, ISBN: 978-0-387-73905-2.

With increasing age of a person refractive errors of the eye occur and are caused substantially by degradation of the eye tissue and in particular of the sclera and cornea. The refractive error might be called, depending on its effect, either Myopia, Hyperopia, Astigmatism or Presbyopia. Myopia is one of the most common new defective visions because of an increasing tallness of mankind resulting in an increasing length of the eyeball. A Keratoconus causing a Hyperopia, for example, is caused by a weakness of the sclera, such that the sclera and cornea are elongated in a certain circular area around the pupil. In any case the occurring weakness of the cornea and sclera is caused by the degradation of the respective collagen tissue of the eye. Conventionally the Keratoconus is either cured by a cornea transplantation or compensated by a hard contact lens. On the other hand also noninvasive treatments for a reconstitution of the cornea and/or sclera are known.

DE 10 2010 020 194 A1 discloses an ophthalmologic Laser therapy system with a Laser light source, wherein the light wavelength is adjusted to induce in the collagen tissue an energy which is just sufficient for inducing a covalent binding but which does not yet cause an ablation or the like. A photosensitizer containing agent such as Riboflavin is said to be not necessary anymore. An optical detector detects cuts in the cornea which are closed and "glued" by the Laser light treatment for stabilizing the cornea. However the light is applied over fields of the cornea or sclera and does not take any orientation of the respective collagen fibers of the tissue into account.

WO 2007 082 127 A2 discloses a combined therapy for a long lasting controlled kerato-reformation, comprising a measurement of the total corneal topography, an ablation of parts of the cornea, optionally a production of a corrective contact lens and a UVA light treatment for growing new crosslinks within the collagen tissue. For the UVA light induced growth of the new crosslinks the photosensitizer Riboflavin is applied in the form of eye drops which increase the amount of the new crosslinks in the cornea. In this way, the biomechanical rigidity or strength of the cornea is increased. The applied light has a wavelength of 365 nm and an intensity of 3 mW/cm$^2$ over 30 minutes. However the microstructure of the collagen is not taken into account.

EP 1 2177 266 A1 by the author of the present invention discloses a Laser therapy system for rejuvenation of the skin via a combined treatment of a first UVA light treatment for collagen crosslinking and a second Laser light treatment with another light source for a subcutaneous Laser needling application. The integrated optical system allows a precise placement of the focus point or light spot, respectively, of the first UVA light and of the second Laser light treatment.

DE 10 2010 022 634 A1 discloses an ophthalmologic Laser therapy system with a pulsed Laser light source, a controllable optical system and a Hartman-Shack sensor, wherein a laser light pulse is positioned and controlled such that the energy is kept constant and at a level for a disruption of the tissue.

WO 2009 033 083 A1 gives a generic view of possible treatments and reactions of the sclera and/or cornea. Treatment of myopia and hyperopia by surgical techniques including corneal interventions, such as reshaping a surface curvature of the cornea, and of non-corneal manipulations, such as altering properties of the sclera, a ciliary muscle, zonules, or the lens, is described. Also a cutting of kerfs into portions of the sclera to improve an accommodation possibility is disclosed. However this increases the risk of infections. A generation of a low-level radiation is preferred for the treatment of the sclera and the ciliary muscle to improve a refraction of the eye, with a light energy not ablating tissue from the sclera or the ciliary muscle. In this document the effects are described rather than a controlled collagen growth within the sclera or cornea.

EP 2 108 347 A1 discloses another ophthalmologic Laser therapy system for a controlled cornea ablation, wherein a surface and thickness of the cornea are detected by an optical coherence tomography system (OCT) and a Laser light beam is controlled in a time-, energy- and space-controlled manner. Thus certain regions of the cornea with irregularities are detected via the OCR and controllably ablated by the Laser beam. The OCR imaging system has a resolution of some 10 μm in the x/y direction and 3 μm in the z direction orthogonal to the surface of the cornea. The process of detecting, controlling and generating the Laser beam happens in real time. However the process takes only an ablation of cornea tissue into account and not a growth of new tissue.

US 2012 059 439 A1 discloses an aberration control by induced new collagen crosslinking combined with a beam shaping technique. It is taught that new collagen crosslinking is used to alter a characteristic of the cornea, such as thickness or refractive index to correct wavefront aberrations. The used light wavelength is 365-370 nm with a light intensity of 3 mW/cm$^2$. However, the UVA light is applied rather as a wide beam over an area of a certain part of the cornea and not as a pattern of a focused light beam. Also, a tightening of the outer sclera to give the eyeball a corrected shape is not mentioned.

A method for skin rejuvenation and strengthening the skin as well as the cornea and sclera in terms of better biomechanical properties such as elasticity and density is by stimulating a new crosslinking within the skin. The crosslinks between the collagen fibers and fiber bundles belong to the substantial components of the collagen tissue structure giving the skin its particular and typical biomechanical properties such as its elasticity and strength. A growth of the new crosslinks between the collagen fibers can be induced by a pretreatment of the skin with the Riboflavin containing and skin penetrating agent in combination with UVA light. The UVA light activates a process similar to a lysyl oxidase process. Lysyl oxidase is an extracellular copper enzyme that catalyzes formation of aldehydes from lysine residues in collagen and elastin precursors. The aldehydes are highly reactive, and undergo spontaneous chemical reactions with other lysyl oxidase-derived aldehyde residues, or with unmodified lysine residues. This results in crosslinking collagen and elastin, which is essential for stabilization of collagen fibrils and for the integrity and elasticity of mature elastin and, last but not least, for the skin. Complex crosslinks are formed in collagen and in elastin that differ in structure (source: Wikipedia). During crosslinking end parts of the collagen fibrils become connected with each other in a kind of covalent connection, wherein the space between the collagen fibrils becomes shorter causing a contraction of the collagen tissue in that region. In other words, if the collagen tissue is contracted in x/y direction and parallel to the skin surface the collagen tissue also grows in thickness in an orthogonal z-direction. An application of a photosensitizes agent containing e.g. Riboflavin in combination with a UVA light stimulates a process similar to the lysyl oxidase process and the crosslinking therewith.

WO 2012/158991 A2 discloses a light therapy treatment device for a controlled application of a crosslinking agent, according to the preamble of claim 1. Said device is adapted for an application of a determined amount of cross-linking agent as function of position, to achieve a growth of new cross-links in certain areas of the eye. However, the light energy is spread and not minimized for a desired growth of the new collagen cross-links.

WO 2012/145159 A1 discloses a light therapy treatment device similar to that of WO 2012/158991 A2, wherein said device is furthermore adapted for measurements of the shape cornea and for a control of the light energy taking into account a feedback signal of the growth of a corneal surface. However, the light energy is still spread and not minimized and controlled locally according to an orientation of the existing collagen fibers or fiber bundles.

However, the induction of the new crosslinks within the collagen tissue by the UVA light must also be seen in view of a toxic effect on the skin as well. Thus, the applied UVA energy has to be reduced as much as possible, such that the desired new crosslinks are generated with minimum UVA energy. Also the collagen tissue could be shaped more precisely and determined by an application of the UVA light within a focus point and by taking a microstructure of the collagen tissue into account.

For clarity reasons the eye is to be understood as a living eye. The UVA light is equivalent to UVA energy or energy density, whatever is correct in the respective sense which is apparent to a person skilled in the art. The UVA light can be a Laser light or another light.

SUMMARY OF THE INVENTION

The objective of the invention is to overcome the shortcomings explained above and to provide a Laser therapy system for a noninvasive correction of the refractive system of the eye and for a reshaping of the eyeball and in particular of the sclera and/or cornea by inducing a growth of new crosslinks within a respective collagen tissue. Another objective is to induce the growth of the new crosslinks with an applied light energy which is as little as possible.

The above objectives as well as further objectives which will also become apparent from the following description are achieved by a Laser therapy system or a respective method for an eye treatment according to the features mentioned in the independent claim 1 or 15, respectively. Additional advantageous features and characteristics of the invention are set forth in the dependent claims and in the detailed description.

Advantageously, the Laser therapy system comprises a processing and control unit which is adapted to determine, based on a current first collagen tissue structure of a sclera and/or cornea, a new second collagen tissue structure, such that the current first collagen tissue structure is strengthened and tightened in certain regions and such that the refractive error of the eye is minimized therewith. Two effects are preferably taken into account and calculated to correct the refractive error.

First, new corrective crosslinks are planned in the sclera to tighten the sclera, such that the eyeball obtains another shape. In other words the eyeball is reshaped, wherein the optical characteristics are modified and changed back to a more optically correct shape, such that the focus point of the light is moved back to the retina.

Secondly an optical density and an optical index of the cornea are taken into account, wherein a growth of the crosslinks therein effects a change in density and a different focal length of the optical system of the eye.

Advantageously the Laser therapy system comprises an imaging unit for 3D imaging of the cornea and/or sclera and an image processing unit which are adapted to recognize a current first collagen tissue structure and an orientation of the respective collagen fibers and collagen fiber bundles therein. Thus, by recognizing the orientation of the collagen fibers, the current first three-dimensional collagen structure of the collagen tissue is recognizable, wherein changes of said structure can be implemented in a determined way. Thus, the Laser therapy system allows not only a global change of the collagen tissue structure by a global growth of new crosslinks, but it allows also a determined growth of the new crosslinks, such that a determined microstructure can be built. Said microstructure can be built in a way, wherein the respective crosslinks can be induced in all three dimensions or directions, depending on the current first collagen tissue structure, existing forces such as the inner pressure of the eye and the definition of how the collagen tissue structure shall be formed. Preferably the Laser therapy system calculates the new shape of the eyeball in order to achieve a minimized refractive error of the eye and then calculates the new crosslinks necessary to achieve said new shape.

Further the Laser therapy system allows a calculation of a necessary change in density of the cornea in order to achieve a new focal length matching with the retina, and in a following step another calculation of the necessary crosslinks in the cornea to achieve said focal length. Then the necessary UVA energy and the respective positions of the focus points for the respective application of said UVA energy are calculated and applied precisely by control of the UVA light source and the deflection and focusing unit. Preferably a density change in the cornea is induced which has a form of a concave or convex lens or a Fresnel lens changing the focal length of the eye.

By the determination of the new crosslinks within a microstructure of the collagen tissue structure the new collagen tissue structure can be shaped and the UVA light energy is evidentially reduced to a minimum necessary to achieve the previously determined or calculated new shape of the collagen tissue structure, or the cornea and/or sclera, respectively.

The orientation of the collagen fibers can be for example a longitudinal, a transverse or a diagonal orientation with respect to a preferred direction. The recognition of the orientation of the collagen fibers within a certain collagen layer allows inducing the growth of the new crosslinks preferably perpendicular to the orientation and as a matrix pattern. Thus, the growth is induced more naturally, with less applied total UVA energy and according to biomechanical forces which the collagen tissue has to withstand. By the 3D imaging unit and the image processing unit as well as by the controllable deflection and focusing unit for the UVA light the current first collagen tissue structure can be formed or shaped in a determined way by the induction of the new crosslinks. Such a precise and determined shaping is obviously not possible without taking the microstructure of the collagen tissue into account. This is a very much distinguishing characteristic of the present invention.

Thus the UVA light energy is preferably positioned stepwise or continuously along a plurality of paths describing a pattern as a dot matrix or a lined matrix in different possible ways and matrix forms, wherein the matrix is adapted to the orientation of the collagen fibers. Thus the matrix can be applied in a same plane as the collagen fibers or in a plane perpendicular thereto or in a volume with a direction aligned with or perpendicular to the collagen fibers. The crosslinks can be grown in a structure exactly adapted to the current first collagen tissue structure, to forces therein and to a new desired shape of the eyeball. It is obvious for a person skilled in the art that the desired shape is achievable with less UVA light energy compared with a less precise application of a different UVA light energy. A cytotoxic effect of the UVA light treatment is obviously reduced.

Using the photosensitizer as an agent for the skin and matching it with UVA light, said growth of the new collagen can be even more increased, or the UVA light energy can be decreased, respectively.

Preferably the Laser therapy system comprises also a second light source being a Laser, to be able to cut certain trenches or to apply a kind of a Laser Needling treatment in the sclera. The Laser Needling treatment induces a growth of new collagen. The Laser Needling is another advantageous treatment for an additional rejuvenation and strengthening of the skin and for a reshaping of the eyeball. As the Laser Needling treatment is preferably achievable with the same Laser therapy system as for the UVA light treatment, the patient does not have to be moved or readjusted from the UVA light treatment system to the Laser Needling system, such that no unnecessary time is lost and the same man-machine interface can be used by the surgeon. No adaptation effort of the user to another device has to be invested. Also, most of the components therein can be reused as the imaging unit, preferably the image processing unit, the optical system and the processing and control unit which are high-tech equipment and very expensive. A combination of the two different treatment technologies and methods with a same treatment objective is a good supplement and completion to correct the refractive system of the eye.

The application of the light energy is preferably provided in an automatic or semi-automatic controlled way, which saves time. Furthermore, such a micro-treatment with the UVA light is also only possible in an automatic or semi-automatic way, and would hardly be possible manually within a reasonable time limit. This becomes also evident in view of the UVA light treatment generating predefined patterns with thousands of single light spots within said focus points per $mm^2$.

With regard to the image processing unit, the UVA light treatment can be applied in a more automatically controlled way and in a manner of micro-treatment which would not be possible by traditional manual treatment practices in a reasonable treatment time. Thus the treatment time can also be reduced in relation to the traditional manual treatment practices, reducing as well the treatment cost.

Further advantageous aspects of the invention are set forth in the following detailed description.

One solution of a preferred embodiment according to the present invention is disclosed in the following drawings and in the detailed description but it shall not be limiting the invention.

DETAILED DESCRIPTION OF A PREFERRED EMBODIMENT OF THE INVENTION

Figure 1:
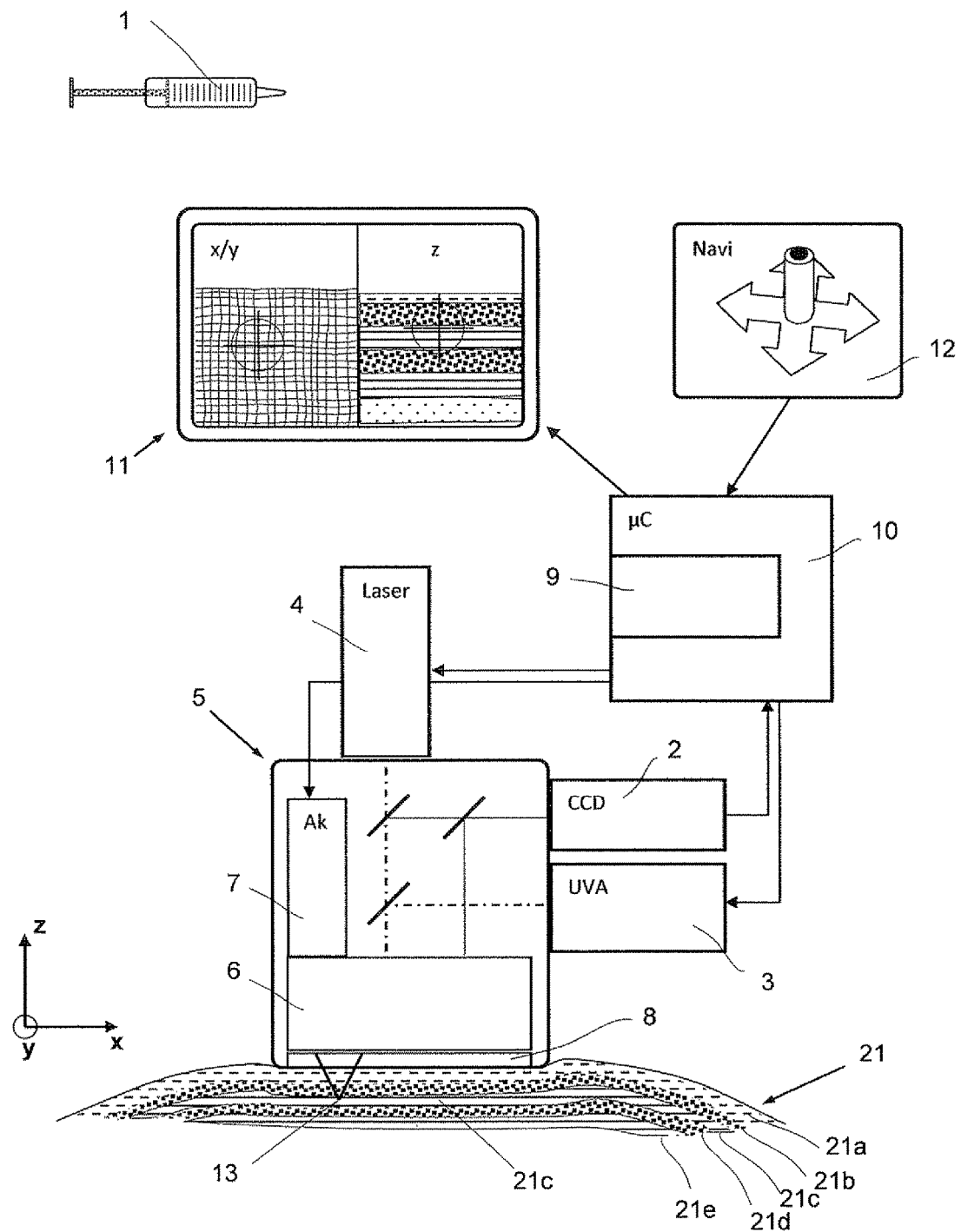
FIG. 1 is a schematic drawing of the Laser therapy system with a UVA light source, another light source, an optical system with an aperture connected to a surface of an eye, a screen, a navigation control input device and a separate dispenser for a photosensitizes containing agent.

FIG. 1 shows a schematic diagram of the laser therapy system for an eye treatment and in particular for a treatment of the sclera 21 and/or cornea 24 of a living eye 20 according to a preferred embodiment of the invention. For the sake of clarity the terms "sclera" 21 and/or "cornea" 24 generally also stand for a part of said sclera and/or cornea. For the sake of brevity the sclera 21 and/or cornea 24 are also simply called skin in the following.

According to the invention, the Laser therapy system comprises a dispenser 1 such as a syringe, for example, containing an agent for an application on the skin, wherein the agent contains a photosensitizer for mediating a collagen and elastin crosslinking in a targeted manner during an UVA light irradiation. For the sake of brevity the word collagen preferably comprises also elastin. Generally, the word collagen also stands for a tissue or tissue structure of collagen fibers, wherein a plurality of collagen fibers connected with each other build up the collagen structure. The photosensitizer containing agent is preferably a cream, a gel or a liquid with a skin penetrating effect and it contains preferably Riboflavin (vitamin B2), coenzymes, vitamin A, vitamin E, or vitamin C or a combination thereof for a synthesis of the collagen and elastin in the skin. Preferably the photosensitizer containing agent comprises also fluorescent properties for determining a penetration depth in the skin. Preferably at least the mucosa is penetrated by the agent. As described above, the photosensitizer agent and a UVA light wavelength are matched with each other, such that an applied UVA light energy causes a maximal effect with a reaction similar to a lysyl oxidase reaction, wherein a crosslinking between end-parts of single collagen fibers is induced and takes place. Preferably the dispenser 1 can also be an integral part of the Laser therapy system. Further it may comprise a sensor for determining a certain quantity of the applied agent.

The Laser therapy system further comprises an imaging unit 2 for a 3D imaging of the skin or respectively of a volume thereof, wherein the imaging unit 2 is coupled to the skin by an optical system 5 and by an aperture 8 thereof. The aperture 8 has preferably a function as an inlet for light coming from the skin which is preferably a reflected light and preferably another function also as an outlet for a possible illumination light for illumination of the skin. Thus a volume of the skin is electronically imaged and respective image data is output. The optical system is preferably controllable in such a way that different volumes of the skin can be imaged within a same position of the aperture 8 relative to the skin or the eye, respectively. Preferably the illumination brightness, the contrast and the like are controllable by another connected component of the Laser therapy system. Preferably the imaging unit 2 is based either on an Optical Coherence Tomography (OCT), a fluorescence or self-fluorescence microscopy, a fluorescence or self-fluorescence tomography, a light reflection or a light extinction measurement or a combination thereof. Preferably the imaging unit 2 comprises a CCD sensor. Preferably the imaging unit 2 works with at least two wavelengths for a better discrimination between the collagen and the blood vessels. Preferably the imaging unit comprises also at least one polarization filter. Another kind of the imaging unit 2 according to the prior art is also imaginable. Preferably a monitor with a screen 11 is connected to the imaging unit 2 either directly or via an image processing unit 9 or another processing and control unit 10. Preferably the skin is displayed on the screen 11 with the current first collagen structure in top view in a left portion, wherein the current first collagen structure from a side view as a cross section at a center point is shown in a right portion of the screen 11. The center part is preferably indicated by a reticle.

The Laser therapy system further comprises the image processing unit 9 which is preferably connected with an output of the imaging unit 2 receiving and further processing the image data of the imaging unit 2. It is also imaginable that the image processing unit 9 receives the image data via a processing and control unit 10. Possibly the image processing unit 9 is also a part of the processing and control unit 10, for example a software module or a separate hardware module or both. The image processing unit 9 is adapted to recognize a current first collagen tissue structure and to recognize therein also an orientation of respective collagen fibrils and fibril bundles. Thus a thickness of the current first collagen tissue structure is preferably also measurable. The current first collagen tissue structure and its thickness are a function of a position. At this point it shall be mentioned that the function and all other functions may be a Cartesian, a polar, a spherical polar coordinate system or the like. The image processing unit 9 is adapted to recognize preferably also one or more different adjacent collagen layers within the skin, wherein the different collagen layers are preferably arranged on top of each other like a sandwich. The image processing unit 9 enhances preferably also a displayed image on the screen 11 by filtering the displayed image, such that a contrast is enhanced, different collagen layers are displayed in different colors, edges are enhanced and the like; features that are already state of the art and known as digital filtering. The image processing unit 9 recognizes preferably the orientation of the respective collagen tissue or fibers or collagen fiber bundles therein. Preferably all adjacent collagen layers with alternating orientations are displayed. Thus a subsequent treatment with the UVA light can be provided in a much more physiologically adapted and correct way. An applied pattern with the UVA light energy for a local area can thus become aligned with said orientation of the collagen fibers. Said alignment is preferably parallel or perpendicular to the orientation or aligned in a different way according to certain expert know-how.

The Laser therapy system further comprises a UVA light source 3, which is controllable and which generates the UVA light or the UVA light energy, respectively. The UVA light source 3 is also connected to the optical system 5, wherein the UVA light is controllably deflected and focused on a focus point 13 behind the aperture 8 which lies in the skin if the aperture 8 is attached to the skin. The focus point 13 of the UVA light can be deflected and focused by the optical system 5, such that the focus point 13 can be controlled in all three directions within at least a part of the imaging volume, wherein the part is preferably 30% or 50% or even 100% of the imaging volume. The UVA wavelength and intensity are adapted to allow the new collagen crosslinking in combination with the photosensitizer agent. Preferably the wavelength and the intensity are matched with the photosensitizer agent and the skin for a most efficient photochemical effect and the collagen crosslinking. The UVA wavelength is preferably set to 340-450 nm. The UVA light has an intensity of preferably 100 µW-100 mW or alternatively an energy output of 2-10 Joule/cm$^2$ or more preferably 0.8-2 Joule/cm$^2$ or even more preferably 0.1-0.8 Joule/cm$^2$. Alternatively the wavelength of the UVA light is 300-450 nm. Alternatively the wavelength is preferably about 260-290 nm, and more preferably 275-285 nm. Another preferable wavelength is about 370 nm. Preferably the UVA light source 3 is a Laser such as for example an LED laser diode. Preferably the UVA light source 3 is also controllable in its light intensity or energy or both. Preferably it can be pulsed, such that a defined light energy is applicable to the skin. Laser pulses can be in a range of fs-ns-µs, but also pulses in the range of ms are imaginable. A use of a UVA light source 3 with a continuous light output is also imaginable, wherein the focus point 13 is positioned and moved by the optical system 5 along certain paths in the skin.

The optical system 5 comprises the optical deflection and focusing unit 6 which is preferably controllable by an actuator unit 7 and deflects and focuses the UVA light of the UVA light source 3 on the focus point 13 behind the aperture 8 and in the skin. The actuator unit 7, which is preferably an integral part of the optical deflection and focusing unit 6, is controllable by electrical signals from the processing and control unit 10. The optical deflection and focusing unit 6 deflects and focuses the UVA light on the focus point 13, such that it is controllably positioned behind the aperture 8 in said imaging volume. The aperture 8 of the optical system 5 comprises preferably an adapter plate which is intended to be positioned on the skin preferably with an optical coupling liquid or coupling gel 8c in between.

Figure 5:
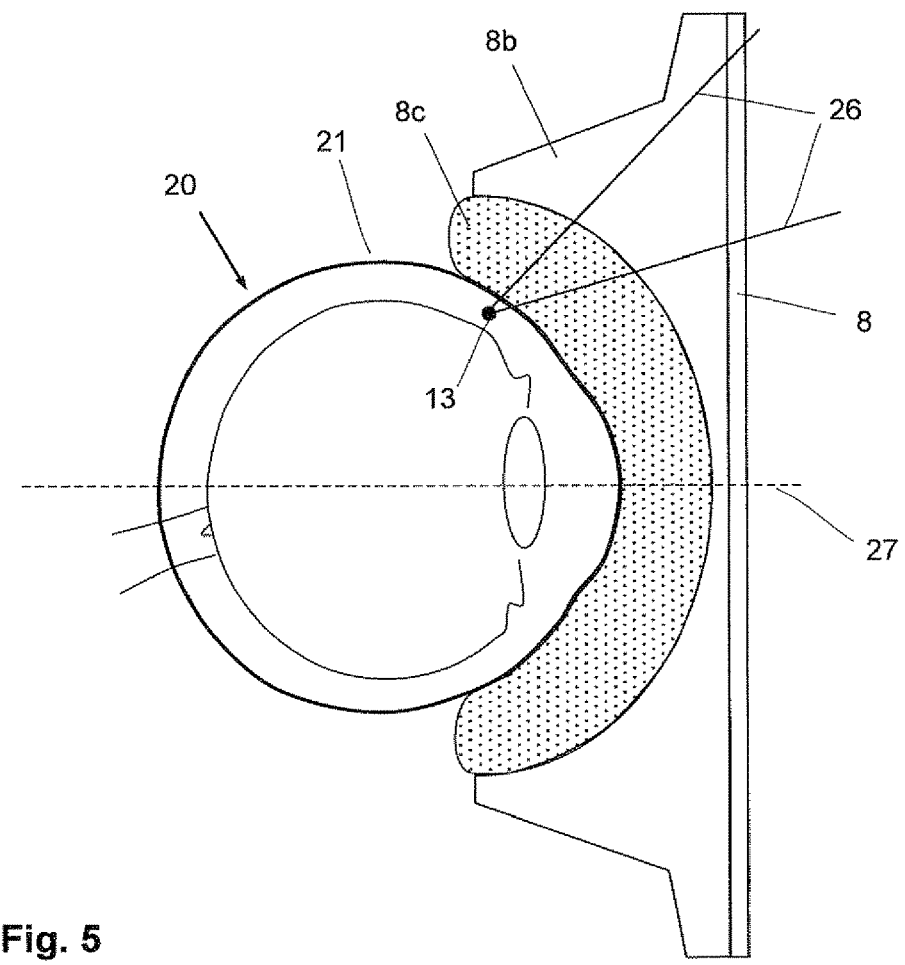
FIG. 5 is a schematic drawing of the eye from a side view with a contact lens connected thereto between the eye and the aperture and with an additional coupling gel to the eye.

FIG. 5 shows the adapter plate connected to the eye 20 as a contact lens 8b, wherein an optical path 26 of the UVA light is shown with the focus point 13. Preferably the contact lens has a concave shape adapted to the eye 20. More preferably the contact lens 8b is optically connected to the eye 20 by a flexible pocket with a liquid inside, by a liquid or by a coupling gel 8c having a functionality as an optical coupling. Preferably the adapter plate or the contact lens 8b comprises a plurality of layers which are connected with each other as integral or non-integral parts. Preferably the contact lens 8b is either of glass or the like or of the coupling gel 8c. The coupling gel is preferably an immersion liquid. Preferably the immersion liquid contains Riboflavin. Via the coupling gel or the immersion liquid a resolution of the image and of the treatment can be increased and a damage of the surface of the eye can be decreased. Preferably the coupling gel or the immersion liquid is pumped into the gap between the eye and the aperture 8. Thus the light path is adapted to a more ideal light path.

Alternatively and/or additionally the aperture 8 comprises a surrounding ring shaped means or container being adapted to be placed on the eye and to be filled with the immersion liquid above the eye, such that the UVA light or the second light is led from the aperture 8 through the immersion liquid towards the eye. Preferably the immersion liquid is a tear fluid. Preferably the immersion fluid comprises Riboflavin.

The photosensitive substance serves as e.g. Riboflavin as well as another immersion means that diffuses into the mucosa of the conjunctives and/or sclera. By using the immersion liquid, as explained above, the optical distance between the objective lens and the image depth is optimized in a sense of a more linear optical path function. Aberrations caused by an adjustment of errors of the diffraction index of the optic system remain constant along the optical axis and the photosensitive substance can be exposed in the entire writing area with identical focus and/or patterns of intensity.

Preferably the optical system has a high numerical aperture of at least 0.4 and more preferably of at least 0.6. The treatment depth is preferably between 0.001 and 2 mm below the surface of the sclera or conjunctiva 21.

Preferably a connecting part of the adapter plate to the eye 20 is soft such as to achieve connecting forces smaller than would substantially change the refractive system of the eye. Preferably the middle part of the contact lens 8b above the cornea is opaque for the UVA light for certain applications.

Figure 6:
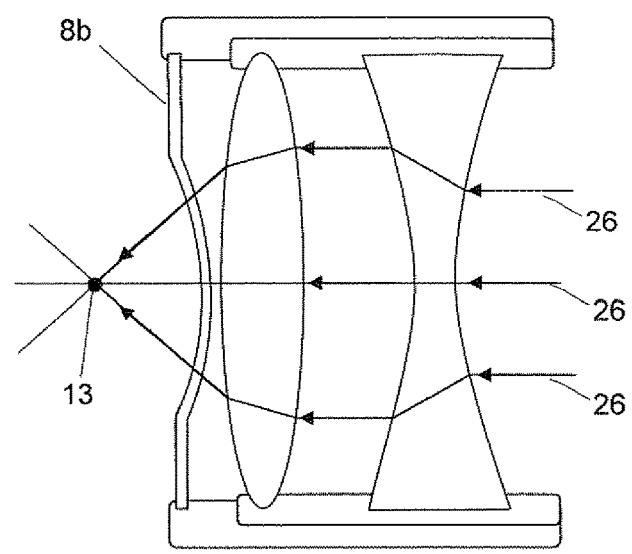
FIG. 6 is a schematic drawing from a side view of another contact lens 8b with a lens system connected thereto.

FIG. 6 shows from a side view another preferred contact lens 8b with a lens system in front of the contact lens 8b. Said lens system comprises preferably a concave or biconcave lens or the like for enlarging the light beam diameter and a convex or biconvex lens or the like to focus the light beam to the focus point 13. The light path 26 is shown as an example. Said lens system comprises preferably a liquid lens which is fast adaptable. Preferably the lens system is adjustable to the focus point 13 via Piezo actuators. Preferably the lens system is moveable in respect to the contact lens 8b along its optical axis.

Preferably the aperture 8 is part of a movable arm or head which is optically connected with the optical system 5, such that the aperture 8 is controllably moveable over the skin either manually or controllably actuated by the processing and control unit 10.

The UVA light is focused in such a way that it enters the skin behind the aperture 8 with a first cross-sectional area of preferably 1-30 mm$^2$, which, however, can also be larger. A second cross-sectional area of the focus point 13, also called a light spot, has a diameter of preferably 10-100 µm. The diameter of the second cross-sectional area can also reach 1 mm. The factor between the first and the second cross-sectional area is preferably in a range of 1-10. More preferably said range is 10-100 and even more preferably said range is 100-1000. The depth of the focus point 13 behind the aperture 8 in the skin is controllable preferably in a range of 0.03-3 mm.

The processing and control unit 10 is adapted to receive data relating to a refractive error of the eye 20 having characteristics of a Myopia, a Hyperopia, an Astigmatism, a Presbyopia, a Keratoconus or the like. Based on the recognized current first collagen tissue structure a second collagen tissue structure is determined with additional new corrective collagen crosslinks by the processing and control unit 10, such as to achieve a minimized refractive error of the eye 20. The current first collagen tissue structure is preferably analyzed for its tissue strength and the forces therein because of the inner pressure of the eyeball and outer pressures. A finite element method or the like may be applied for this purpose. Thus, the new corrected second collagen tissue structure is determined, such that the shape of the eyeball is changed and all refractive errors are minimized. Preferably the cornea is also analyzed in terms of how far its collagen tissue structure can be changed as well, for instance including tissue density changes such that regions with higher or lower tissue densities are generated in order to obtain a kind of optical lens. It is imaginable, for instance, that a more dense region in the cornea can be generated by the UVA light induced new crosslinks therein. Thus a region with an increased density is preferably created in the form of a concave or convex lens or a Fresnel lens or the like.

Further the processing and control unit 10 is adapted to calculate or determine the UVA light energy as a function of the position, of the new corrective collagen crosslinks and of a growth factor for the new corrective collagen crosslinks. A certain pattern of how the UVA light is to be applied as a dot or line matrix pattern or the like is also taken into account. The growth factor for the new corrective collagen crosslinks is preferably derived from a database and an expert system, wherein the best matching growth factor for a patient is determined and selected for the subsequent calculations of the UVA energy. Preferably the growth factor is also dependent on the amount of the new corrective crosslinks per volume unit. An appropriate pattern for the focus point 13 and for the plurality of UVA light energies or the UVA energy as a function, respectively, which are to be applied in the skin, is preferably also determined as a function of the collagen tissue structure.

Further the processing and control unit 10 is adapted to control the UVA light source 3 and the deflection and focusing unit 6 of the optical system 5, such that the determined UVA light energy and the position of the focus point 13 are generated in the skin. The UVA light energy and the position of the focus point 13 are preferably controlled in an automatic or semi-automatic way along the determined positions or paths or as the pattern. Any manual input is preferably provided via navigation control input means 12. The navigation control input means 12 may be a joystick with buttons, a keyboard, a touch pad, a touch screen, a mouse or a combination thereof.

FIG. 1 further shows the focus point 13 positioned within the skin which is the sclera 21 or cornea 24 and more precisely on top of the collagen layer 21c. The skin consists in the given example of a plurality of skin layers 21a-21e which are partly collagen layers.

Furthermore the preferred Laser therapy system of FIG. 1 comprises also a second light source which is a Laser light source 4 which is controllable as well and generates a second light with a second wavelength. Preferably the second light source outputs a second intensity or alternatively a second energy or energy pulses. Preferably a switchable Laser is used. The second light source is also connected to the optical system 5, wherein the second light is controllably deflected and focused on the focus point 13 behind the aperture 8 and in the skin. The focus point 13 of the second light can be deflected and focused by the optical system 5, such that the focus point 13 can be controlled in all three directions within at least a second part of the imaging volume, wherein the second part is preferably 30% or 50% or even 100% of the imaging volume.

The second wavelength, the second light intensity or energy, a second pulse duration and a second pulse frequency or repetition rate, respectively, of the second light source are preferably adapted for a good absorption within the skin. The second light is preferably adapted for releasing energy in the focus point 13 so as to make end-arterioles of the sclera permeable, preferably in a targeted manner with as little collateral damage as possible. Preferably, Laser parameters are adapted and set in such a way that in the focus point 13 in the skin either a thermal, a photoablative or a plasma-induced reaction are produced. The second wavelength is preferably 450-550 nm, particularly preferred 550-650 nm or 650-800 nm or 800-2000 nm in the IR range. The second wavelength is preferably selected and set such that the second wavelength is absorbed particularly well by blood vessels and by hemoglobin and as little as possible by the other tissue of the skin. The second light intensity preferably corresponds to 1 mW-100 W as a focused light beam. The second pulse duration preferably is 10 ps-100 µs, but it can also be set to be shorter or longer with respective energy pulses. Preferably the imaging unit 2 and the image processing unit 9 are adapted to recognize also the end-arterioles.

The focus point 13 and the applied UVA light energy are preferably positioned stepwise or continuously along a plurality of paths describing a pattern as a dot matrix or a lined matrix. The dot matrix or line matrix with the plurality of paths are disposed either:

in the form of parallel, orthogonally intersecting or circular paths within a plane or a spherical plane within the current first collagen tissue structure;

in the form of parallel, orthogonally intersecting or circular paths within a plurality of planes or spherical planes adjacent and parallel to each other within the current first collagen tissue structure;

in the form of parallel, orthogonally intersecting or circular paths within a collagen layer of the current first collagen tissue structure;

in the form of parallel, orthogonally intersecting or circular paths within two or more collagen layers, wherein the collagen layers are locally parallel to the surface of the eye; or in the form of a three-dimensional pattern adapted to the current first collagen tissue structure.

For the sake of clarity, the term "plane" comprises also spherical planes or planes within a spherical polar coordinate system.

Preferably the processing and control unit 10 is adapted to align the pattern within the respective collagen layer with the orientation of the respective collagen fibers within the respective collagen layer.

Preferably the processing and control unit 10 is further adapted to generate a crosslink pattern like a concave or convex lens or like a Fresnel lens.

Figure 2:
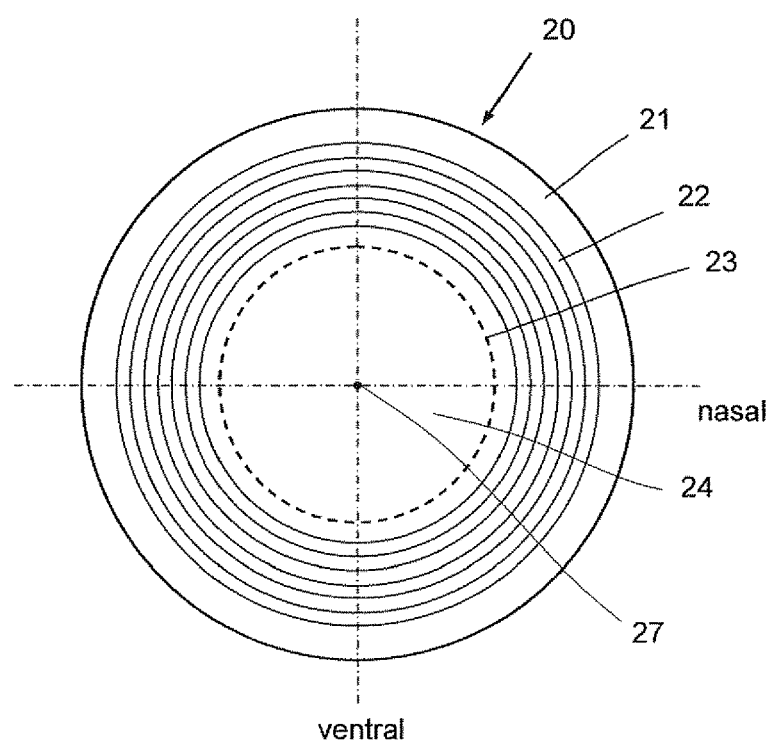
FIG. 2 is, in the upper part, a schematic drawing of the eye from a frontal view indicating a limbus and circular rings around a center axis of the eye, wherein the lower drawing indicates areas with different thicknesses of the sclera.
Figure 2:
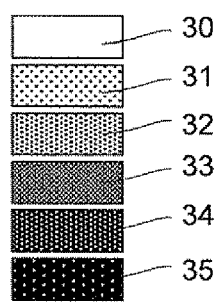
Figure 2:
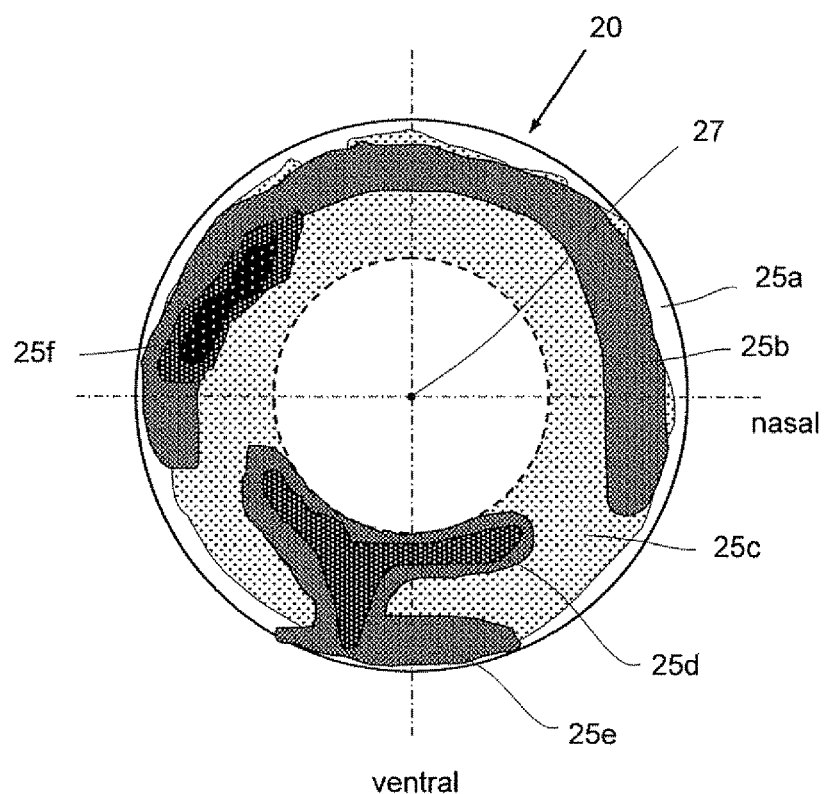

FIG. 2 shows, in its upper part, a schematic drawing of the eye 20 from a frontal view in the direction of the center axis 24 of the eye 20, showing the sclera 21 and the cornea 24, indicating the limbus 23 and around the center axis 27 a plurality of the circular ring shaped areas 22 which are preferably defined for calculation purposes.

FIG. 2 shows, in its bottom part, another schematic drawing of the eye 20 in the same view from the front but with indicated different thicknesses of the collagen tissue in different regions 25a-f. FIG. 2 shows, on the left side, an indication table with textures corresponding to the different thickness values 30-35. The texture is also indicated in the different regions 25a-f. The thickness is displayed on the screen 11 preferably as in FIG. 2, bottom part, but in different colors or the like.

Figure 3:
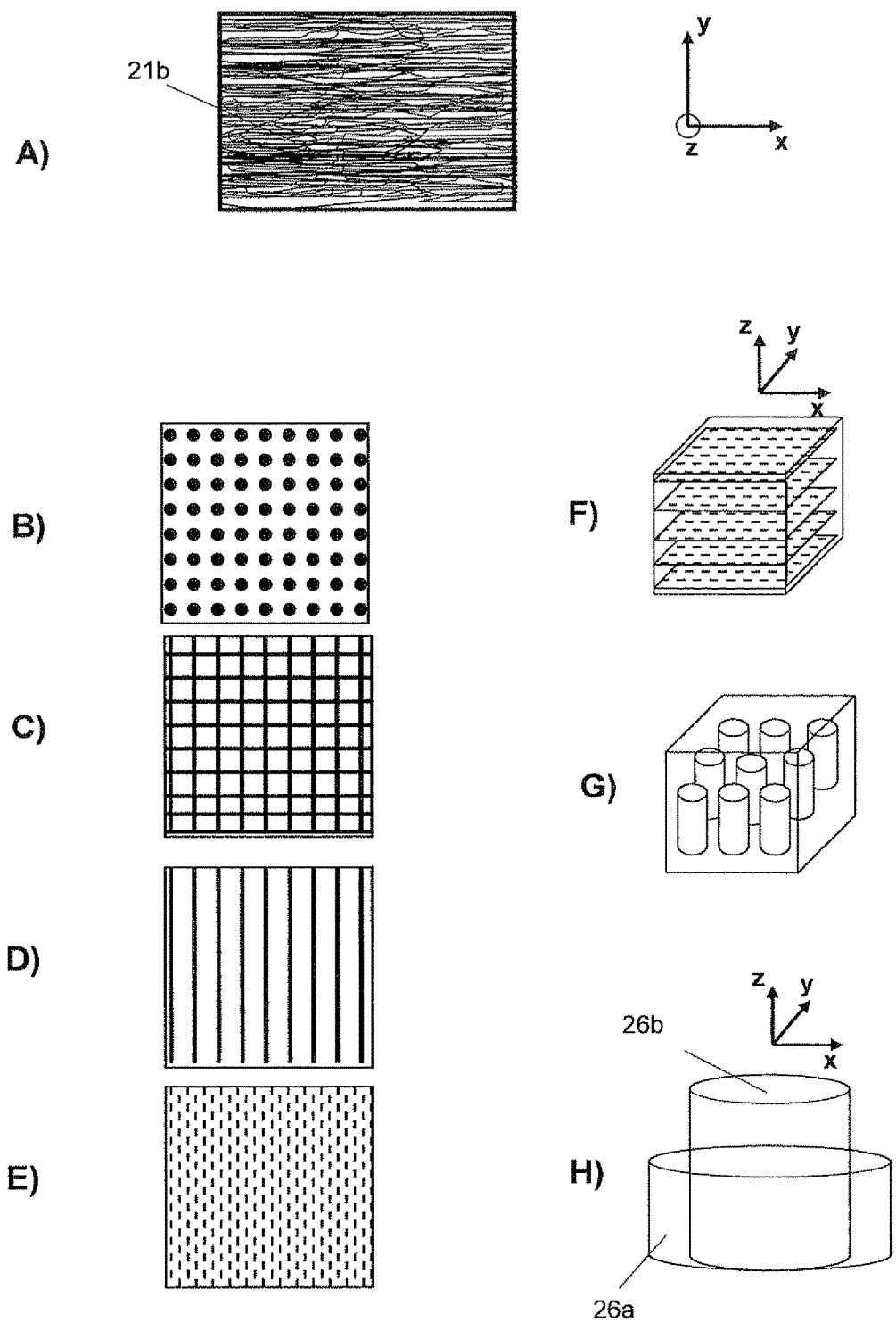
FIG. 3A is a schematic drawing of a top view of a collagen layer of the sclera and/or cornea showing an orientation of the respective collagen fibers or fiber bundles.
FIGS. 3B-G are schematic drawings of different patterns for an application of a UVA light energy in the sclera and/or cornea.
FIG. 3H is a schematic drawing of a skin volume before and after a treatment with the UVA light energy.

FIG. 3A is a schematic drawing of a top view of a certain collagen layer 21b of the sclera 21 or cornea 24, wherein the orientation of the collagen fibers or the collagen fiber bundles is recognizable. The depicted collagen layer is preferably a cross-sectional cut part of the collagen tissue structure at any location and in any direction.

FIGS. 3B-3G show schematically some examples of the pattern described above as a dot or line matrix. FIGS. 3F-G are examples of a three-dimensional perspective, wherein in FIG. 3F a plurality of planes each containing a certain part of the pattern or in FIG. 3G three-dimensional cylindrical parts of the pattern are arranged within the certain volume of the skin. The distances of the focus points 13 and light spots, respectively, according to FIG. 3B are preferably determined such that the distance is short enough to allow a crosslinking between the adjacent collagen fibrils and big enough to reduce the total UVA energy applied to a reasonable amount. In this example the UVA energy is about 20% of the energy which would be applied if no focusing and blank areas would exist.

FIG. 3H is the schematic drawing of the skin volume 26a before the treatment and of the skin volume 26b after the treatment with the UVA light energy. It shows that the volume of the skin remains equal but that the shape changes or shrinks depending on the induced or produced crosslinks in said volume.

Preferably the image processing unit 9 is adapted to detect continuously the collagen tissue structure and the growth of the new corrective collagen crosslinks, wherein the processing and control unit 10 determines and adapts the UVA light energy continuously. Thus the determined new crosslinks are achieved in a controlled way.

Preferably the Laser therapy system comprises also means for a measurement of the refractive system and a current refractive error of the eye 20, wherein said measurement is undertaken repetitively during the UVA light treatment.

Furthermore the processing and control unit 10 is adapted a) to determine and adapt continuously the necessary new collagen tissue structure with the new corrective collagen crosslinks in order to achieve a minimized refractive error taking a latest status of the refractive system and the new crosslinks into account; and b) to determine the currently necessary UVA light energy again for the current new crosslinks. Preferably the growth factor is also measured and adapted to the eye.

Preferably the processing and control unit 10 is adapted to determine the new collagen tissue structure by taking a tightening and an elasticity of the sclera into account, such that the eyeball receives another shape due to the new corrective collagen crosslinks.

Preferably the processing and control unit 10 is further adapted to determine the new collagen tissue structure by taking a change of a density of the cornea with a different optical index due to the new corrective collagen crosslinks into account.

Preferably the image processing unit 9 and/or the processing and control unit 10 are adapted to detect and to determine at least one reference point within the cornea and/or the sclera 21 and to use said at least one reference point for image stitching or to refer detected and measured values to the at least one reference point. Preferably the UVA light energy is referred to said at least one reference point.

Figure 4:
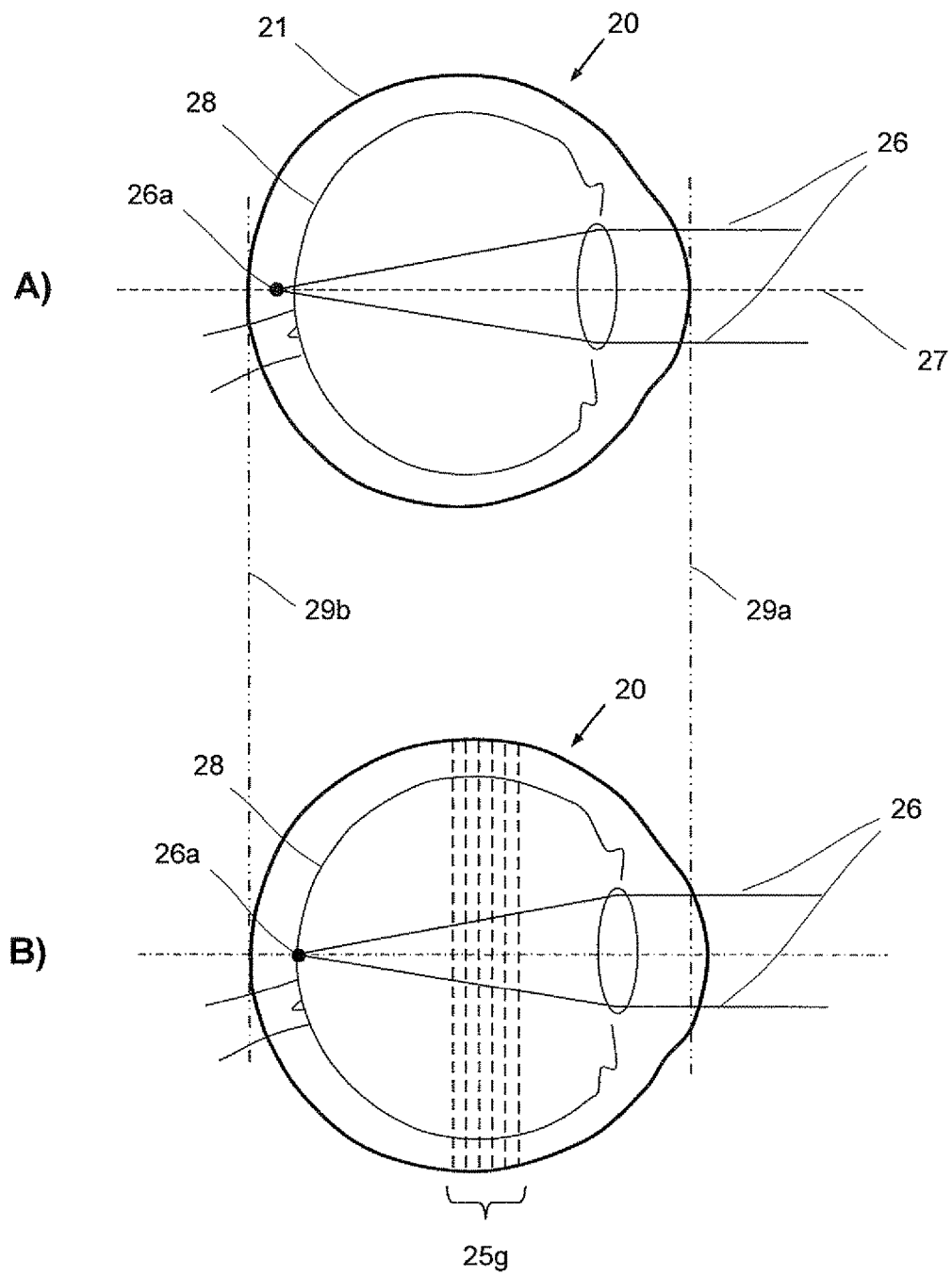
FIG. 4A is a schematic drawing of a cross-sectional side view of the eye with a refractive error, wherein the focal length is too long.
FIG. 4B is a schematic drawing of a cross-sectional side view of the eye, wherein a region of the sclera is indicated and treated with UVA light, such that the focal length is corrected.

FIG. 4A shows a schematic drawing of a cross-sectional side view of the eye 20 with a center axis 27 of the eye 20, an optical path 26 and a retinal focus point 26a which lies outside the retina 28. In other words the focal length is too high and needs to be shortened by a tightening of an annular region 25g of the sclera 21.

FIG. 4B shows a schematic drawing of a cross-sectional side view of the eye 20 after a treatment with the UVA light energy in the indicated annular region 25g of the sclera 21. The demarcation lines 29a/29b show that the eye has obtained a shorter shape and the focal length with its retinal focus point 26a has been corrected therein and matches the retina 28.

Preferably the UVA light is generated by two different light beams with a wavelength double the wavelength of the generated UVA light, such that the two different light beams or photons overlap within a few femto-seconds and generate substantially the UVA light with the half wavelength. Preferably the resulting wavelength of the UVA light lies between 300-450 nm. Preferably the UVA light source 3 is a light source for a one photon excitation. For a two photon excitation with the respective two different light beams or photons the respective light source is a femto-second laser.

Preferably the Laser light source 4 is a femto-second Laser with a resulting second wavelength as mentioned before.

It shall be mentioned again, that the recognition of the collagen fibers within the skin and growth of the new collagen is preferably detected three-dimensionally.

A Method for treatment of the cornea and sclera 21 of the eye for the noninvasive correction of its refractive system uses the Light therapy system as described above, wherein the method comprises the following steps:

a) dispensing the agent containing the photosensitizer on the cornea and sclera 21;

b) recording 3D images of the cornea and sclera 21 within an imaging volume by the imaging unit 2 of the Light therapy system adapted thereto and outputting image data;

c) recognizing the first collagen tissue structure within the image data and further recognizing the first orientation of the respective collagen fibers or collagen fiber bundles within the first collagen tissue structure as a function of position, by the image processing unit 9 of the Light therapy system adapted thereto and outputting respective processed image data;

d) receiving the data relating to a refractive error of the eye 20;

e) determining the second collagen tissue structure with additional new corrective collagen crosslinks added to the first collagen tissue structure by the processing and control unit 10 of the Light therapy system being adapted thereto, such as to achieve a minimized refractive error of the eye 20;

f) determining a UVA light energy as a function of position of the new corrective collagen crosslinks and of the growth factor for the new corrective collagen crosslinks under the UVA light energy by the processing and control unit 10 of the Light therapy system, such that the growth of the new corrective collagen crosslinks is effected;

g) applying the determined UVA light energy to the cornea and sclera 21 by the UVA light source 3 and an optical system 5 of the Light therapy system, such that UVA light of the UVA light source 3 is focused to a focus point 13, and the focus point 13 is controllably moved along lines or along a net of lines which correlates with the first orientation of the respective collagen fibers or collagen fiber bundles.

Preferably in step g) the focus point 13 is moved stepwise or continuously along a plurality of paths describing the pattern as the dot matrix or the lined matrix, wherein the plurality of paths are disposed in the form of parallel, orthogonally intersecting or circular paths within a plane or a spherical plane within the first collagen tissue structure.

Preferably in step g) the focus point 13 is moved stepwise or continuously along a plurality of paths describing a pattern as a dot matrix or a lined matrix, wherein the plurality of paths are disposed in the form of parallel, orthogonally intersecting or circular paths within a plurality of planes or spherical planes adjacent and parallel to each other within the first collagen tissue structure.

Preferably in step g) the focus point 13 is moved stepwise or continuously along a plurality of paths describing a pattern as a dot matrix or a lined matrix, wherein the plurality of paths are disposed in the form of parallel, orthogonally intersecting or circular paths within a collagen layer of the first collagen tissue structure.

Preferably in step g) the focus point 13 is moved stepwise or continuously along a plurality of paths describing a pattern as a dot matrix or a lined matrix, wherein the plurality of paths are disposed in the form of parallel, orthogonally intersecting or circular paths within two or more collagen layers, wherein the collagen layers are locally parallel to the surface of the eye.

Preferably in step g) the focus point 13 is moved stepwise or continuously along a plurality of paths describing a pattern as a dot matrix or a lined matrix, wherein the plurality of paths are disposed in the form of a three-dimensional pattern adapted to the first collagen tissue structure.

Preferably within a further step endarteriols are detected within the image data by the image processing unit 9, and then a second light of the Laser light source 4 is applied to the eye being focused to the focus point 13, wherein said focus point 13 is controllably moved by the processing and control unit 10 to the determined endarteriols, wherein the second light is applied with a second energy which is adapted to denature or perforate the end-arteriole or to induce an optical breakdown in order to make the end-arteriole permeable for corpuscular blood cells and to stimulate a growth of collagen. Such a procedure is known in the field of dermatology as Laser-Needling.

REFERENCE NUMERALS 1 dispenser
2 imaging unit
3 UVA light source
4 Laser light source
5 optical system
6 optical deflection and focusing unit
7 actuator unit
8 aperture
8b contact lens
8c coupling gel
9 image processing unit
10 processing and control unit
11 screen
12 navigation control input means
13 focus point
20 eye
21 sclera
21a-21e skin layer
22 ring shaped area
23 limbus
24 cornea
25a-g region
26 optical path
26a retinal focus point
27 center axis of the eye 20
28 retina
29a-b demarcation line
X, Y, Z coordinates

The invention claimed is:

1. Light therapy system for a treatment of the cornea and sclera for a noninvasive correction of a refractive system of an eye, comprising:
   a) a dispenser for dispensing an agent containing a photosensitizer on the cornea and sclera;
   b) an imaging unit for 3D imaging of the cornea and sclera within an imaging volume, outputting image data;
   c) an image processing unit being adapted to receive the image data, to recognize a first collagen tissue structure;
   d) a UVA light source which is controllable and generates UVA light with a first wavelength which is adapted to activate a crosslinking in the cornea and sclera in combination with the photosensitizer dispensed on the cornea and sclera;
   e) an optical system coupled to the imaging unit and to the UVA light source, the optical system having an aperture to the eye as an outlet for the UVA light coming from the UVA light source and as an inlet for light irradiated from the imaging volume in the cornea or sclera being guided by the optical system to the imaging unit, the optical system providing a controllable deflection and focusing means for deflecting and focusing the UVA light from the UVA light source to a focus point behind the aperture, such that said focus point is controllably positioned within the imaging volume; and
   f) a processing and control unit adapted to control the optical system and the UVA light source;
characterized in that
   g) the image processing unit is adapted to recognize a first orientation of respective collagen fibers or collagen fiber bundles within the first collagen tissue structure as a function of position;
   h) the processing and control unit is adapted
      to receive data relating to a refractive error of the eye;
      to determine a second collagen tissue structure with additional new corrective collagen crosslinks added to the first collagen tissue structure, such as to achieve a minimized refractive error of the eye;
      to determine a UVA light energy as a function of the position, the new corrective collagen crosslinks and a growth factor for the new corrective collagen crosslinks, such that the growth of the new corrective collagen crosslinks is effected; and
      to control the optical system and the UVA light source, such that the determined UVA light energy is applied within the cornea and sclera along the first orientation of the respective collagen fibers or collagen fiber bundles.

2. Light therapy system according to claim 1, wherein the focus point for the application of the UVA light energy is positioned stepwise or continuously along a plurality of paths describing a pattern as a dot matrix or a lined matrix, wherein the plurality of paths are disposed
   in the form of parallel, orthogonally intersecting or circular paths within a plane or a spherical plane within the first collagen tissue structure;
   in the form of parallel, orthogonally intersecting or circular paths within a plurality of planes or spherical planes adjacent and parallel to each other within the first collagen tissue structure;
   in the form of parallel, orthogonally intersecting or circular paths within a collagen layer of the first collagen tissue structure;
   in the form of parallel, orthogonally intersecting or circular paths within two or more collagen layers, wherein the collagen layers are locally parallel to the surface of the eye; or
   in the form of a three-dimensional pattern adapted to the first collagen tissue structure.

3. Light therapy system according to claim 2, wherein the processing and control unit is adapted to align the pattern within a respective collagen layer with the first orientation of the respective collagen layer.

4. Light therapy system according to claim 2, wherein the processing and control unit is further adapted to generate a crosslink pattern like a Fresnel lens.

5. Light therapy system according to claim 1, wherein the image processing unit is adapted to detect continuously the collagen tissue structure and the growth of the new corrective collagen crosslinks, and the processing and control unit determines and adapts the UVA light energy continuously, such that the respective new crosslinks are achieved in a controlled way.

6. Light therapy system according to claim 1, further comprising means for a measurement of the refractive system and a current refractive error of the eye, wherein the refractive error is measured repetitively during the UVA light treatment; and the processing and control unit is further adapted to determine and adapt continuously the second collagen tissue structure with the new corrective collagen crosslinks, such as to achieve a minimized refractive error of the eye according to a current status of the current refractive error of the eye.

7. Light therapy system according to claim 1, wherein the processing and control unit is further adapted to determine the second collagen tissue structure by taking a tightening and an elasticity of the sclera into account, such that the eyeball obtains a different shape due to the new corrective collagen crosslinks.

8. Light therapy system according to claim 1, wherein the processing and control unit is further adapted to determine the second collagen tissue structure by taking a change in density of the cornea with a different optical index due to the new corrective collagen crosslinks into account.

9. Light therapy system according to claim 1, wherein the imaging unit is based either on an Optical Coherence Tomography (OCT), a fluorescence or self-fluorescence microscopy, a fluorescence or self-fluorescence tomography, a light reflection or a light extinction measurement with one or more wavelengths for discrimination between collagen and blood vessels, comprises polarization filters, or is a combination thereof.

10. Light therapy system according to claim 1, wherein the image processing unit and/or the processing and control unit are adapted to detect and to determine at least one reference point within the cornea and/or the sclera and to use said at least one reference point for image stitching or to refer the UVA light energy to said at least one reference point and the eye.

11. Light therapy system according to claim 1, wherein the agent is a cream, a gel or a liquid with the effect of penetrating the skin and contains riboflavin (vitamin B2), and/or wherein the agent contains coenzymes for a synthesis of collagen and elastin, namely vitamin A, vitamin E and/or vitamin C, and/or wherein the photosensitizer containing agent is fluorescent for determining the penetration depth into the skin, and/or wherein the aperture comprises an integral or a non-integral contact lens for an optical coupling with the eye, wherein a side of the contact lens directed towards the eye has a concave form adapted to the eye and being either of glass or of a coupling gel or of a flexible pocket with a liquid or a coupling gel inside as to optically adapt to the eye in a soft way with connecting forces smaller than would substantially change the refractive system of the eye, and/or wherein the aperture comprises an integral or a non-integral contact lens for an optical coupling with the eye, wherein a middle part of the contact lens above the cornea is opaque for the first and the second light, and/or wherein the aperture comprises a surrounding ring shaped means or container being adapted to be placed on the eye and to be filled with an immersion liquid above the eye, such that the UVA light or another light is led from the aperture through the immersion liquid towards the eye.

12. Light therapy system according to claim 1, further comprising a second light source as a Laser light source which is controllable and generates a second light with a second wavelength, a second intensity or energy being adapted to be absorbed by the cornea and/or sclera for effecting a photoablation, wherein the second light source is connected to the optical system, such that the second light exits behind the aperture and is focused on the focus point being deflectable, positionable and controllable by the processing and control unit.

13. Light therapy system according to claim 12, wherein the imaging unit and the image processing unit are adapted to further recognize end-arterioles within the imaging volume of the sclera; and the processing and control unit is further adapted to apply the focus point with a respective second energy at the respective end-arteriole, such that the end-arteriole is denatured or perforated or an optical breakdown is induced in order to make the end-arteriole permeable for corpuscular blood cells and to stimulate a growth of collagen (Laser-Needling).

14. Light therapy system according to claim 1, wherein the processing and control unit is further adapted so that the focus point can be repositioned and the UVA energy is applicable either manually by a navigation control input means, automatically or semi-automatically.

* * * * *